United States Patent [19]  
Henkelmann et al.

[11] Patent Number: 5,543,568  
[45] Date of Patent: Aug. 6, 1996

[54] PREPARATION OF α,β-UNSATURATED β-OXYCARBOXYLIC ACID CHLORIDES

[75] Inventors: Jochem Henkelmann, Mannheim; Lutz Tietze, Goettingen, both of Germany

[73] Assignee: BASF Aktiengesellschaft, Ludwigshafen, Germany

[21] Appl. No.: 117,315

[22] Filed: Sep. 7, 1993

[30] Foreign Application Priority Data

Sep. 10, 1992 [DE] Germany .......................... 42 30 283.8

[51] Int. Cl.⁶ .................................................. C07C 51/58
[52] U.S. Cl. ........................................... 562/861; 562/857
[58] Field of Search .................................... 562/857, 865

[56] References Cited

U.S. PATENT DOCUMENTS

| 2,449,471 | 9/1948 | Gresham | 260/484 |
| 2,464,747 | 3/1949 | Grosser | 260/90 |
| 2,768,174 | 10/1956 | Paul et al. | 260/345.1 |
| 4,239,888 | 12/1980 | Miller | 544/309 |
| 4,996,995 | 10/1990 | Chodorge et al. | 562/861 |

FOREIGN PATENT DOCUMENTS

| 1073479 | 1/1960 | Germany . |
| 158462 | 7/1961 | Germany . |
| 3415475 | 11/1985 | Germany . |

OTHER PUBLICATIONS

CA58:5654c 1963.
CA78(5):29282g 1972.
CA81(25)164631e 1974.
*Heterocycles*, vol. 16, p. 1515, 1981.
Can. J. Chem., vol. 63, p. 2787, 1985.
J. Med. Chem., vol. 26, p. 1075, 1983.
J. Heterocycl. Chem., vol. 13, p. 1015, 1976.
J. Chem. Soc. PT. I, p. 1241, 1976.
Aust. J. Chem., vol. 30, p. 459, 1977.
Zhur. Org. Khim., vol. 2, p. 66, 1966.
Can. J. Chem. vol. 44, p. 661, 1966.
Chem. Listy., vol. 47, p. 413, 1953.
J. Org. Chem., vol. 27, p. 3083, 1962.
J. Chem. Soc., PT I, p. 1169 (1959).
J. Org. Chem., vol. 27, p. 3317, 1962.
Chem. Ber., vol. 98, p. 2260, 1965.
Houben–Weyl, bol. 8/3, 4th Ed., pp. 425–427; 543–547; and 655–658.

*Primary Examiner*—Paul J. Killos
*Attorney, Agent, or Firm*—Keil & Weinkauf

[57] ABSTRACT

A process for the preparation of α,β-unsaturated β-oxycarboxylic acid chlorides of the formula I $$R^1O-\underset{\underset{}{|}}{\overset{\overset{R^2}{|}}{C}}=\underset{\underset{}{|}}{\overset{\overset{R^3}{|}}{C}}-COCl \quad \text{I}$$

where $R^1$ is a C-organic radical, and $R^2$ and $R^3$, independently of one another, are hydrogen or a C-organic radical, comprises carrying out the addition reaction of an enol derivative of the formula II $$R^1O-\underset{\underset{}{|}}{\overset{\overset{R^2}{|}}{C}}=\overset{\overset{R^3}{|}}{CH} \quad \text{II}$$

with a compound of the formula IIIa, IIIb or IIIc $$Cl-CO-CO \quad \text{IIIa}$$

$$Cl-\overset{\overset{O}{\|}}{C}-OCCl_3 \quad \text{IIIB}$$

$$Cl_3CO-\overset{\overset{O}{\|}}{C}-OCCl_3 \quad \text{IIIc}$$

and converting the resultant acid chloride of the formula $$R^1O-\underset{\underset{Cl}{|}}{\overset{\overset{R^2}{|}}{C}}-\underset{\underset{H}{|}}{\overset{\overset{R^3}{|}}{C}}-COCl \quad \text{IV}$$

into I by elimination of hydrogen chloride (HCl).

15 Claims, No Drawings

PREPARATION OF α,β-UNSATURATED β-OXYCARBOXYLIC ACID CHLORIDES

The present invention relates to a process for the preparation of α,β-unsaturated β-oxycarboxylic acid chlorides of the formula I

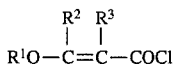

where $R^1$ is a C-organic radical, and $R^2$ and $R^3$, independently of one another, are hydrogen or a C-organic radical.

The present invention furthermore relates to α,β-unsaturated β-oxycarboxylic acid chlorides of the formula Ia $$R^aO\text{—}CR^b\text{=}CR^c\text{—}COCl \qquad Ia$$

where $R^a$ is substituted or unsubstituted benzyl, and $R^b$ and $R^c$, independently of one another, are hydrogen or substituted or unsubstituted $C_1$–$C_8$-alkyl, $C_3$–$C_8$-alkenyl, $C_3$–$C_8$-alkynyl, $C_3$–$C_8$-cycloalkyl or $C_5$–$C_8$-cycloalkenyl, a substituted or unsubstituted, 3- to 8-membered, saturated or monounsaturated ring system which, in addition to carbon ring members, may contain one to three heteroatoms from the group consisting of nitrogen, oxygen and sulfur, substituted or unsubstituted phenyl, 1-naphthyl or 2-naphthyl, or a substituted or unsubstituted 5-membered aromatic ring system which, in addition to carbon ring members, contains an oxygen or sulfur atom.

α,β-unsaturated β-oxycarboxylic acids and derivatives thereof are valuable intermediates in organic synthesis (Heterocycles 16 (1981) 1515; Can. J. Chem. 63 (1985) 2787; J. Med. Chem. 26 (1983) 1075; J. Heter. Chem. 13 (1976) 1015; J. Chem. Soc., Perkin Trans. I, 1241 (1976); Aust. J. Chem. 30 (1977) 459; Zhur. org. Khim. 2 (1966) 66; Can. J. Chem. 44 (1966) 661).

They are obtained, for example, by ester condensation (to give the β-keto derivative) and subsequent enolization in accordance with the reaction scheme below:

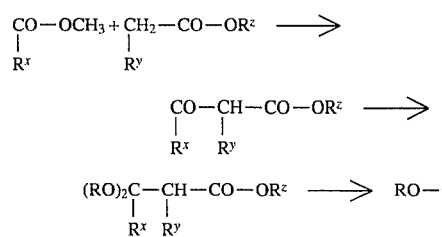

(eg. Zhur. org. Khim. 2 (1966) 66).

Another possibility is to react an orthoformate with an α-halocarboxylic ester followed by elimination:

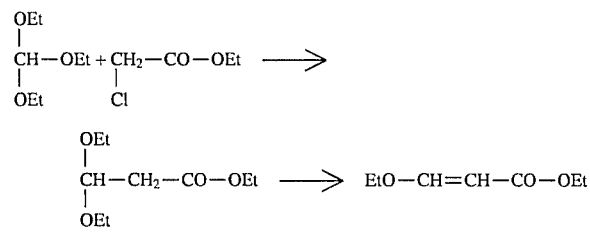

(eg. J. Med. Chem. 26 (1983) 1075–1076).

Another possibility is to react an orthoformate with ketene followed by elimination:

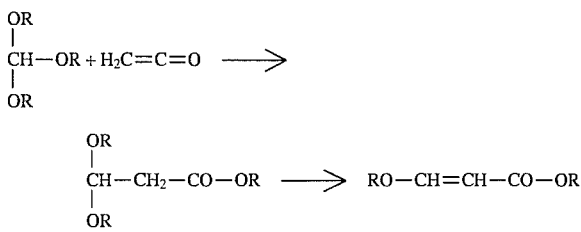

(R=eg. Me, Et) (DK-A 158 462 (1990)=CA 113, 190761w (1990); F. Sorm and J. Smrt, Chem. Listy 47 (1953) 413–417=CA 49, 175c (1955); D. G. Crosby and R. V. Berthold, J. Org. Chem. 27 (1962) 3083–85; U.S. Pat. No. 2,449,471 (1948)=CA 43 (1949)

Another possibility is to condense an acetic ester with CO followed by alkylation of the condensation product:

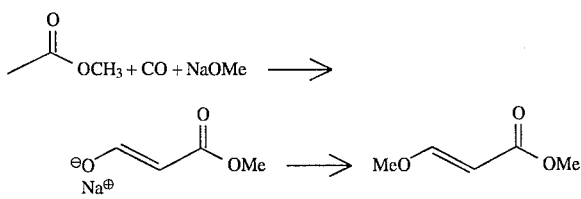

(DE-A 34 15 475)

Activated derivatives of α,β-unsaturated β-oxycarboxylic acids, for example the chlorides, can be prepared by hydrolyzing the ester and chlorinating the sodium salt of the acid:

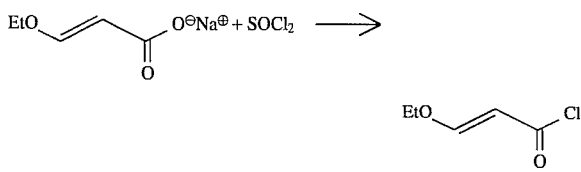

(J. Chem. Soc. 1959, 1169–78)

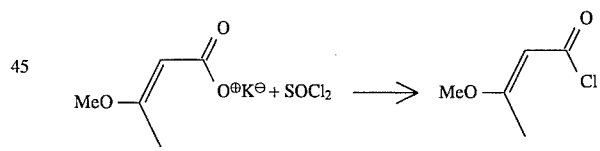

(J. Org. Chem. 27 (1962) 3317–3319) or by chlorinating the free acid

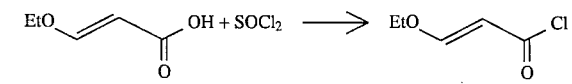

(U.S. Pat. No. 4,239,888).

A significant disadvantage of the known methods is due to the fact that conversion of the resultant esters into activated carboxylic acid derivatives, such as halides, can only be carried out by complex (multi-step) syntheses.

A direct preparation method comprises reacting vinyl ethers with phosgene:

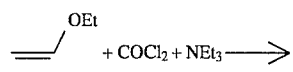

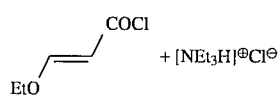

(U.S. Pat. No. 2,768,174 and SU-A 462,145)

The triethylamine can also be replaced by other nitrogen bases, eg. pyridine or diethylaniline. The hydrogen chloride formed during the reaction can also be bound by addition reaction with allyl chloride (SU-A 462 145). The reaction is not selective. The principal byproduct is formed by the addition reaction of HCl with the particular vinyl ether (U.S. Pat. No. 2,768,174):

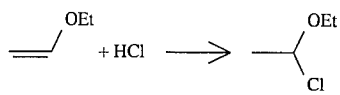

The amine hydrochloride formed must be separated off as a solid in a complex manner, and the dichloropropane formed in the scavenging reaction of HCl with allyl chloride is difficult to dispose of.

In addition, mixtures of vinyl ethers and phosgene tend toward spontaneous polymerization (U.S. Pat. No. 2,464,747).

Furthermore, the preparation of carboxylic acids, other esters and amides is difficult due to the requisite reaction conditions during these reactions, in particular with respect to thermally unstable radicals, and the known processes therefore do not allow broad access to compounds of this type.

The literature furthermore discloses that oxalyl chloride adds to two equivalents of vinyl ether at room temperature:

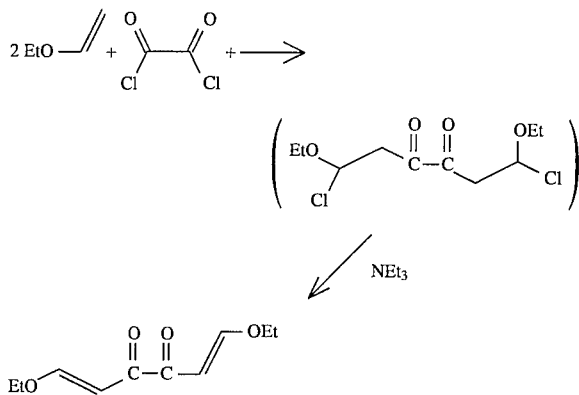

(Chem. Ber. 98 (1965) 2260–2265)

The bisaddition product formed initially is thermally unstable and decomposes spontaneously. It can be converted into the stable 1,4-bisethoxymethylene-2,3-butanedione by elimination with triethylamine.

In the same way, other vinyl ethers also react with oxalyl chloride, eg. 5,6-dihydro-4H-pyran.

It is an object of the present invention to provide a technically simple and economical process for the preparation of α,β-unsaturated β-oxycarboxylic acids and activated derivatives thereof, in particular the halides.

We have found that this object is achieved by a process for the preparation of α,β-unsaturated β-oxycarboxylic acid chlorides of the formula I

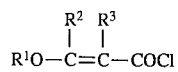

where $R^1$ is a C-organic radical, and $R^2$ and $R^3$, independently of one another, are hydrogen or a C-organic radical, which comprises carrying out the addition reaction of an enol derivative of the formula II

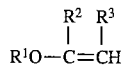

with a compound of the formula IIIa, IIIb or IIIc

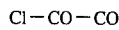    IIIa

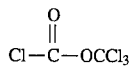    IIIB

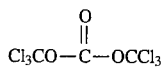    IIIc and converting the resultant acid chloride of the formula IV

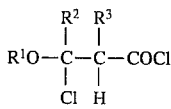    IV into I by elimination of hydrogen chloride (HCl).

In general, the novel process is carried out by first carrying out the addition reaction of a chloride of the formula IIIa, IIIb or IIIc with an enol derivative of the formula II at from −78° to 100° C., preferably at from −10° to 80° C., in particular at from 20° to 60° C., forming the corresponding acid chloride of the formula IV.

The reaction can be carried out without using solvents or diluents if the reactants are liquid at the reaction temperature. However, it is also possible to carry out the reaction in an aprotic solvent or diluent.

Examples of suitable solvents or diluents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, and ethers, such as diethyl ether, diisopropyl ether, tert-butyl methyl ether, dioxane, anisole and tetrahydrofuran, and nitriles, such as acetonitrile and propionitrile.

It is also possible to use mixtures of said solvents.

The reaction is particularly preferably carried out without solvents or in aromatic hydrocarbons, such as toluene, as solvent.

Reactants II and III are generally reacted with one another in a molar II:IIIa/IIIb/IIIc ratio of from 0.1:1 to 1:1, preferably from 0.2:1 to 0.8:1, in particular from 0.4:1 to 0.6:1.

Since the halides III and the resultant acid chloride IV are moisture-labile, it is advisable to carry out the reaction with exclusion of water, preferably under a protective-gas atmosphere (nitrogen or another inert gas).

In the case of the reaction of II with IIIb or IIIc, it may be advantageous to accelerate the reaction by adding catalytic amounts of a tertiary amine, such as triethylamine or pyridine.

The acid chloride IV obtained in this way eliminates hydrogen chloride (HCl) at from 30° to 80° C., forming the corresponding α,β-unsaturated β-oxycarboxylic acid chloride I.

For this step of the reaction, it may be advantageous to remove the resultant hydrogen chloride from the reaction volume, either by means of a slightly reduced pressure or by passing inert gas through the reaction mixture or the reaction vessel and thus removing the hydrogen chloride formed.

The excess chloride of the formula IIIa, IIIb or IIIc can be fed back into the synthesis (phosgene) and must always be separated off in order to isolate the pure valuable product. The same applies to any catalysts added.

The reaction mixtures obtained in this way are worked up in a conventional manner by distillation.

However, they can also be converted directly (without further purification) into carboxylic acids, esters or amides in a manner known per se:

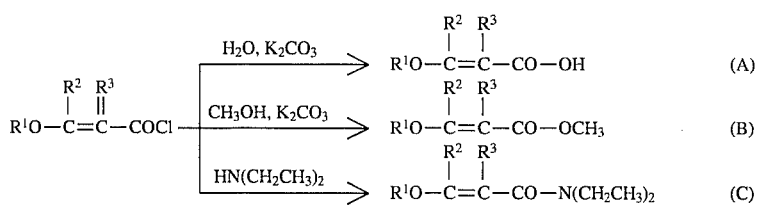

Reactions (A), (B) and (C) are known in general terms (for example Houben-Weyl, 4th Edition, Vol. 8/3, pp. 425–427, 543–547 and 655–658 (Stuttgart, 1952); U.S. Pat. No. 4,239,888).

Due to trans-elimination of hydrogen chloride, the α,β-unsaturated β-oxycarboxylic acid chlorides obtainable by the novel process are predominantly formed as E-isomers of the double bond ($R^1O$ group to carbonyl group).

The carboxylic acid chlorides IIIa, IIIb and IIIc are known. In general, economic considerations mean that preference is given to the compound IIIa (phosgene).

The enol component of the formula II is a compound where $R^1$ is a C-organic radical, for example a substituted or unsubstituted alkyl group, cycloalkyl group, alkenyl group, cycloalkenyl group, aryl group, heterocyclyl group or heteroaryl group;

$R^2$ and $R^3$, independently of one another, are hydrogen or a C-organic radical, for example a substituted or unsubstituted alkyl group, cycloalkyl group, alkenyl group, cycloalkenyl group, alkynyl group, aryl group, heterocylyl group or heteroaryl group.

As far as is known to date, substituents on the abovementioned C-organic radicals have no effect on the course of the reaction. In general, suitable substituents on the C-organic radicals are those which do not themselves have basic or acidic properties, for example halogen atoms, nitro groups, cyano groups, ester groups, carbonyl groups, ether groups or thioether groups.

In particular, C-organic radicals are taken to mean the following:

$C_1$–$C_6$-alkyl, in particular $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

$C_3$–$C_8$-alkenyl, in particular $C_3$–$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl;

$C_3$–$C_8$-alkynyl, in particular $C_3$–$C_6$-alkynyl, such as 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl-2,2-dimethyl-3-butynyl, 1-ethyl-2-butynyl, 1-ethyl-3-butynyl, 2-ethyl-3-butynyl and 1-ethyl-1-methyl-2-propynyl;

$C_3$–$C_8$-cycloalkyl, such as cyclopropyl, cyclobutyl, cyclopentyl, cyclohexyl, cycloheptyl and cyclooctyl;

$C_5$–$C_8$-cycloakenyl, such as cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclooct-1-enyl, cyclooct-2-enyl, cyclooct-3-enyl and cyclooct-1-enyl;

a 3- to 8-membered, saturated or monounsaturated ring system which, in addition to carbon ring members, may contain one to three heteroatoms from the group consisting of oxygen and sulfur, preferably 5- to 6-membered, saturated or unsaturated heterocyclic rings containing one to three oxygen or sulfur atoms, such as 2-tetrahydrofuryl, 3-tetrahydrofuryl, 2-tetrahydrothienyl, 3-tetrahydrothienyl and tetrahydrotriazin-3-yl;

aryl, such as phenyl, 1-naphthyl or 2-naphthyl;

heteroaryl, such as 5-membered aromatic rings which, in addition to carbon ring members, contain one oxygen or one sulfur atom, such as 2-furyl, 3-furyl, 2-thienyl and 3-thienyl.

The abovementioned C-organic radicals may themselves be partially or fully halogenated, ie. hydrogen atoms bonded to carbon may be replaced by halogen atoms, such as fluorine, chlorine, bromine and iodine, preferably fluorine, chlorine and bromine, in particular fluorine and chlorine. These C-organic radicals may additionally or instead also carry one to three of the following substituents:

cyano; nitro;

$C_1$–$C_4$-alkoxy, such as methoxy, ethoxy, propoxy, 1-methylethoxy, butoxy, 1-methylpropoxy, 2-methylpropoxy and 1,1-dimethylethoxy;

$C_1$–$C_4$-haloalkoxy, in particular $C_1$–$C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy;

$C_1$–$C_4$-alkylthio, such as methylthio, ethylthio, propylthio, 1-methylethylthio, butylthio, 1-methylpropylthio, 2-methylpropylthio and 1,1-dimethylethylthio;

$C_1$–$C_4$-haloalkylthio, in particular $C_1$–$C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio;

$C_3$–$C_8$-cycloalkyl, such as cyclopropyl, cyclobutyl, cyclopentyl, cyclohexyl, cycloheptyl and cyclooctyl;

$C_3$–$C_8$-cycloalkoxy, such as cyclopropoxy, cyclobutoxy, cyclopentoxy, cyclohexoxy, cycloheptoxy and cyclooctoxy;

$C_3$–$C_8$-cycloalkylthio, such as cyclopropylthio, cyclobutylthio, cyclopentylthio, cyclohexylthio, cycloheptylthio and cyclooctylthio:

phenyl, which may be partially or fully halogenated and which, in addition, may carry one to three of the following radicals: cyano, nitro, $C_1$–$C_4$-alkyl as described above, $C_1$–$C_4$-haloalkyl as described above, $C_1$–$C_4$-alkoxy as described above, $C_1$–$C_4$-haloalkoxy as described above, $C_1$–$C_4$-alkylthio as described above and $C_1$–$C_4$-haloalkylthio as described above.

The cyclic C-organic radicals may furthermore carry one to three of the following substituents: $C_1$–$C_4$-alkyl, such as methyl, ethyl, propyl, 1-methylethyl, butyl, 1-methylpropyl, 2-methylpropyl and 1,1-dimethylethyl; $C_1$–$C_4$-haloalkyl, in particular $C_1$–$C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl.

The compounds I are valuable intermediates in the synthesis of active ingredients in the areas of pharmaceuticals and crop protection, for the synthesis of dyes and for the synthesis of polymers (for example J. Org. Chem. 27 (1965) 3083–3085; J. Heterocycl. Chem. 13 (1976) 1015–1020; U.S. Pat. No. 4,239,888; J. Org. Chem. 27 (1965) 3317–3319; J. Chem. Soc. 1959, 1169–1178).

EXAMPLES

Example 1

3-Ethoxyacryloyl chloride 110 g (1.1 mol) of phosgene were introduced at 35° C. over the course of 1.5 hours into a solution of 72 g (1 mol) of ethyl vinyl ether in 100 g of toluene. The mixture was subsequently stirred at 60° C. for a further 4 hours. During the entire experiment time, phosgene and ethyl vinyl ether were condensed back into the reaction mixture by means of a dry-ice condenser at −78° C. The solution was then stripped at room temperature until phosgene-free, and the solvent was removed by distillation. Vacuum distillation at 36° C./70.4 mbar gave 88 g (66%) of valuable product.

Example 2

3,4-Dihydropyran-3-carbonyl chloride 125 g (1.25 mmol) of phosgene gas were introduced over the course of 2.5 hours at 45°–50° C. into a solution of 84 g (1 mol) of 5,6-dihydro-4H-pyran in 50 g of toluene. The mixture was subsequently stirred at 60° C. for a further 5 hours. Work-up was carried out as described in Example 1. Vacuum distillation at 76° C./1 mbar gave 103.9 g (80%) of valuable product.

Example 3

The experiment described under Example 2 was repeated, but the phosgene was introduced at 60° C. over the course of 6 hours. The mixture was subsequently stirred at 60° C. for a further 2 hours. Work-up gave 118.2 g (91%) of valuable product.

Example 4

3-Methoxy-3-methacryloyl chloride 70 g (0.7 mol) of phosgene were introduced at 60° C. over the course of 1.5 hours into a solution of 36 g (0.5 mol) of 2-methoxypropene in 90 g of toluene. The mixture was subsequently stirred at 60° C. for a further 2 hours. Work-up by distillation at 50° C./3 mbar gave 55.8 g (83%) of valuable product.

Example 5

3-Cyclohexyloxyacryloyl chloride 50 g (0.5 mol) of phosgene were condensed into a stirred apparatus fitted with a −78° C. dry-ice condenser. 50.5 g (0.4 mol) of cyclohexyl vinyl ether were subsequently added dropwise at 20° C. over the course of 3 hours. The mixture was subsequently stirred at 50° C. for a further 5 hours. The excess phosgene was expelled by means of nitrogen, and the crude product was worked up by distillation at 110° C./2.5 mbar, giving 66.4 g (88%) of valuable product.

Example 6

3-Cyclohexyloxyacryloyl chloride 12.5 g (0.1 mol) of cyclohexyl vinyl ether were added dropwise at room temperature over the course of 45 minutes to 13.5 g (0.068 mol) of trichloromethyl chloroformate (diphosgene). The mixture was stirred at room temperature for a further 2.5 hours and subsequently heated at 50° C. for 5 hours. The excess phosgene formed during the reaction was expelled by means of nitrogen, and the crude product was worked up by distillation at 110° C./2.5 mbar, giving 13.2 g (70%) of valuable product.

Example 7

3-Cyclohexyloxyacryloyl chloride

In a method similar to that of Example 6, 30 g (0.1 mol) of bis(trichloromethyl) carbonate (triphosgene) were dissolved in 50 ml of toluene and reacted with 34 g (0.27 mol) of cyclohexyl vinyl ether at 15° C. over the course of 45 minutes. The mixture was subsequently stirred at room temperature for a further 2 hours and then heated at 50° C. for 5 hours. The excess phosgene formed during the reaction was expelled by means of nitrogen, and the solvent was removed by distillation. The valuable product was then worked up by distillation similarly to Example 6, giving 38.7 g (76%) of valuable product.

We claim:

1. A process for the preparation of α,β-unsaturated β-oxycarboxylic acid chlorides of the formula I $$R^1O-C(R^2)=C(R^3)-COCl \qquad \text{I}$$

where $R^1$ is a C-organic radical, and $R^2$ and $R^3$, independently of one another, are hydrogen or a C-organic radical, which consists essentially of carrying out the addition reaction of an enol derivative of the formula II $$R^1O-C(R^2)=CH(R^3) \qquad \text{II}$$

with a compound of the formula IIIa, IIIb or IIIc $$Cl-CO-CO \qquad \text{IIIa}$$

$$Cl-\overset{O}{\overset{\|}{C}}-OCCl_3 \qquad \text{IIIB}$$

$$Cl_3CO-\overset{O}{\overset{\|}{C}}-OCCl_3 \qquad \text{IIIc}$$

and converting the resultant acid chloride of the formula IV $$R^1O-\underset{\underset{Cl}{|}}{C}(R^2)-\underset{\underset{H}{|}}{C}(R^3)-COCl \qquad \text{IV}$$

into I by elimination of hydrogen chloride (HCl).

2. A process as claimed in claim 1, wherein the elimination reaction of IV to give I is carried out at from 30° to 80° C.

3. A process as claimed in claim 1, wherein the reactions are carried out without isolation of the intermediates (in situ).

4. A process as claimed in claim 1, wherein the hydrogen chloride (HCl) formed during the elimination is removed from the reaction mixture.

5. A process as claimed in claim 1, wherein the elimination is carried out under reduced pressure.

6. A process for the preparation of acid chlorides of the formula IV as claimed in claim 1, wherein an addition reaction is carried out between an enol derivative of the formula II $$R^1O-C(R^2)=CH(R^3) \qquad \text{II}$$

and a compound of the formula IIIa, IIIb or IIIc as defined in claim 1.

7. A process as claimed in claim 1, wherein the precursors II and IIIa, IIIb or IIIc are reacted with one another in a molar II:IIIa/IIIb/IIIc ratio of from 0.1:1 to 1:1.

8. A process as claimed in claim 1, wherein the reaction of II with IIIa, IIIb or IIIc is carried out at from −78° to 40° C.

9. A process as claimed in claim 1, wherein $R^1$ is substituted or unsubstituted alkyl, cycloalkyl, alkenyl, cycloalkenyl, alkynyl, aryl, heterocyclyl or heteroaryl; and $R^2$ and $R^3$, independently of one another, are hydrogen or substituted or unsubstituted alkyl, cycloalkyl, alkenyl, cycloalkenyl, alkynyl, aryl, heterocyclyl or heteroaryl.

10. A process as claimed in claim 9, wherein $R^1$ is substituted or unsubstituted $C_1$–$C_8$-alkyl, $C_3$–$C_8$-alkenyl, $C_3$–$C_8$-alkynyl, $C_3$–$C_8$-cycloalkyl or $C_5$–$C_8$-cycloalkenyl, a substituted or unsubstituted, 3- to 8-membered, saturated or monounsaturated ring system which, in addition to carbon ring members, may contain one to three heteroatoms from the group consisting of nitrogen, oxygen and sulfur, substituted or unsubstituted phenyl, 1-naphthyl or 2-naphthyl, a substituted or unsubstituted, 5-membered aromatic ring system which, in addition to carbon ring members, contains one oxygen or one sulfur atom, or a substituted or unsubstituted, 6-membered aromatic ring system which, in addition to carbon ring members, contains one to three nitrogen atoms; and $R^2$ and $R^3$, independently of one another, are hydrogen or substituted or unsubstituted $C_1$–$C_8$-alkyl, $C_3$–$C_8$-alkenyl, $C_3$–$C_8$-alkynyl, $C_3$–$C_8$-cycloalkyl or $C_5$–$C_8$-cycloalkenyl, a substituted or unsubstituted, 3- to 8-membered, saturated or monounsaturated ring system which, in addition to carbon ring members, may contain one to three heteroatoms from the group consisting of nitrogen, oxygen and sulfur, substituted or unsubstituted phenyl, 1-naphthyl or 2-naphthyl, or a substituted or unsubstituted, 5-membered aromatic ring system which, in addition to carbon ring members, contains an oxygen or sulfur atom.

11. An α,β-unsaturated β-oxycarboxylic acid chloride of the formula Ia $$R^aO-CR^b=CR^c-COCl \qquad \text{Ia}$$

where $R^a$ is substituted or unsubstituted benzyl, and $R^b$ and $R^c$, independently of one another, are hydrogen or substituted or unsubstituted $C_1$–$C_8$-alkyl, $C_3$–$C_8$-alkenyl, $C_3$–$C_8$-alkynyl, $C_3$–$C_8$-cycloalkyl or $C_5$–$C_8$-cycloalkenyl, a substituted or unsubstituted, 3- to 8-membered, saturated or monounsaturated ring system which, in addition to carbon ring members, may contain one to three heteroatoms from the group consisting of nitrogen, oxygen and sulphur, substituted or unsubstituted phenyl, 1-naphthyl or 2-naphthyl, or a substituted or unsubstituted, 5-membered aromatic ring system which, in addition to carbon ring members, contains an oxygen or sulfur atom.

12. An α,β-unsaturated β-oxycarboxylic acid chloride of the formula Ia as claimed in claim 11, in which the double bond has the E configuration.

13. The process of claim 1, wherein the enol derivative is reacted with a compound of the formula IIIa, as defined in claim 1.

14. The process of claim 1, wherein the enol derivative is reacted with a compound of the formula IIIb, as defined in claim 1.

15. The process of claim 1, wherein the enol derivative is reacted with a compound of the formula IIIc, as defined in claim 1.

* * * * *

UNITED STATES PATENT AND TRADEMARK OFFICE
CERTIFICATE OF CORRECTION

PATENT NO.: 5,543,568

DATED: August 6, 1996

INVENTOR(S): HENKELMANN et al.

It is certified that error appears in the above-identified patent and that said Letters Patent is hereby corrected as shown below:

Column 9, claim 1, line 30, "Cl—CO—CO" should read -- Cl—CO—Cl --.

Signed and Sealed this

Fifth Day of November, 1996

Attest:

BRUCE LEHMAN

Attesting Officer

Commissioner of Patents and Trademarks